(12) United States Patent
Christensen et al.

(10) Patent No.: US 9,752,080 B2
(45) Date of Patent: Sep. 5, 2017

(54) PROCESS FOR PRODUCING HYDROCARBONS

(71) Applicant: Haldor Topsøe A/S, Lyngby (DK)

(72) Inventors: Thomas Sandahl Christensen, Lyngby (DK); Ole Frej Alkilde, Valby (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 14/771,849

(22) PCT Filed: Mar. 25, 2014

(86) PCT No.: PCT/EP2014/055965
§ 371 (c)(1),
(2) Date: Sep. 1, 2015

(87) PCT Pub. No.: WO2014/154691
PCT Pub. Date: Oct. 2, 2014

(65) Prior Publication Data
US 2016/0024391 A1    Jan. 28, 2016

(30) Foreign Application Priority Data
Mar. 27, 2013 (WO) .................. PCT/EP2013/056559

(51) Int. Cl.
*C10G 2/00* (2006.01)
*C01B 3/38* (2006.01)
(Continued)

(52) U.S. Cl.
CPC ................ *C10G 2/32* (2013.01); *C01B 3/382* (2013.01); *C01B 3/386* (2013.01); *C07C 5/03* (2013.01); *C07C 7/148* (2013.01); *C10G 47/00* (2013.01); *C10G 65/12* (2013.01); *C10K 3/026* (2013.01); *C01B 2203/0244* (2013.01);
(Continued)

(58) Field of Classification Search
CPC .......... C10G 2/32; C10G 65/12; C10G 47/00; C07C 7/148; C07C 5/03; C10K 3/026; C01B 3/382; C01B 3/386; C01B 2203/0244; C01B 2203/1052;
(Continued)

(56) References Cited

U.S. PATENT DOCUMENTS 4,481,305 A    11/1984  Jorn et al.
5,146,032 A *  9/1992  Harandi .................... C07C 1/20
                                                              585/312
(Continued)

FOREIGN PATENT DOCUMENTS

CN    1938401 A     3/2007
CN    101223103 A   7/2008
(Continued)

OTHER PUBLICATIONS

Nielsen et al, Technologies for large-scale gas convertsion, 2001, Applied catalyst, 221 379-387.*
Petersen et al, Recent developments in Authothermal reformig and Preforming for Synthesis gas production in GTL applications, 2002, Fuel Chemistry Division Preprints, 47 (1), 96-97.*
J. M. Fox, "The Different Catalytic Routes for Methane Valorization: An Assessment of Processes for Liquid Fuels", Catalysis Reviews: Science and Engineering, Marcel Dekker Inc. New York, US, vol. 35, No. 2, Jun. 1, 1993 pp. 169-212.

*Primary Examiner* — Randy Boyer
*Assistant Examiner* — Juan Valencia
(74) *Attorney, Agent, or Firm* — Blank Rome LLP

(57) ABSTRACT

The invention relates to a process for the production of liquid hydrocarbons by the use of light-end fractions from downstream synthesis in the reforming section of the plant.

12 Claims, 1 Drawing Sheet

(51) Int. Cl.
  *C10G 47/00* (2006.01)
  *C10G 65/12* (2006.01)
  *C10K 3/02* (2006.01)
  *C07C 5/03* (2006.01)
  *C07C 7/148* (2006.01)
(52) U.S. Cl.
  CPC .. *C01B 2203/062* (2013.01); *C01B 2203/063* (2013.01); *C01B 2203/1052* (2013.01); *C01B 2203/1058* (2013.01); *C01B 2203/127* (2013.01); *C01B 2203/1241* (2013.01); *C01B 2203/1247* (2013.01); *C01B 2203/1264* (2013.01); *C10G 2300/1022* (2013.01); *C10G 2300/4081* (2013.01); *C10G 2400/02* (2013.01)
(58) Field of Classification Search
  CPC .... C01B 2300/1022; C01B 2203/1247; C01B 2203/063; C01B 2203/127
  See application file for complete search history.

(56) References Cited

U.S. PATENT DOCUMENTS

| | | |
|---|---|---|
| 2006/0006099 A1* | 1/2006 | Espinoza ............... C10G 47/36 208/108 |
| 2010/0036186 A1 | 2/2010 | Joensen et al. |
| 2013/0065974 A1 | 3/2013 | Kresnyak |

FOREIGN PATENT DOCUMENTS

| | | | |
|---|---|---|---|
| CN | 101568620 A | | 10/2009 |
| EP | 1 526 165 A1 | | 4/2005 |
| NL | EP 2687577 | * | 1/2014 |
| WO | WO 01/60773 A1 | | 8/2001 |
| WO | WO 2009/008092 A1 | | 1/2009 |
| WO | WO 2013/033812 A1 | | 3/2013 |

* cited by examiner

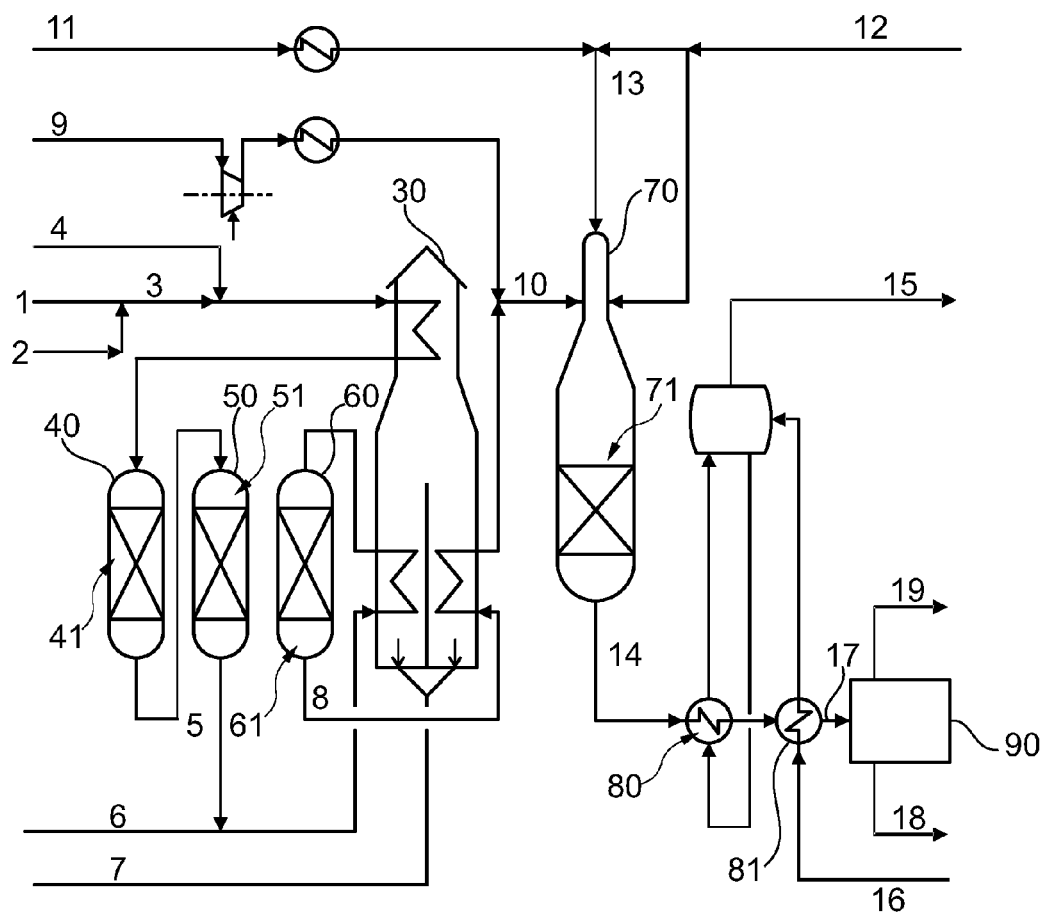

PROCESS FOR PRODUCING HYDROCARBONS

FIELD OF THE INVENTION

The present invention relates to a process for production of synthesis gas used for the production of liquid hydrocarbons, such as diesel and gasoline. The invention relates in particular to a process for the production of liquid hydrocarbons in the form of diesel in which the light-end fraction from the upgrading section downstream the Fischer-Tropsch synthesis of a gas-to-liquid (GTL) diesel process is recycled to the reforming section of the plant. More particularly the entire light-end stream is recycled back to the reforming section upstream desulfurization and before steam addition, in which the reforming section comprises desulfurization, pre-reforming, autothermal reforming (ATR) or catalytic partial oxidation (CPO), without using a steam methane reformer (SMR). In particular, the light-end stream is Liquefied petroleum gas (LPG). The invention encompasses also the recycle of light-end fraction of a GTL gasoline process to the reforming section of the plant.

BACKGROUND OF THE INVENTION

As used herein GTL diesel process means Fischer-Tropsch synthesis in which synthesis gas is converted into liquid hydrocarbons via Fischer-Tropsch reactions, while GTL gasoline process means a process in which synthesis gas is first converted to oxygenated compounds such as methanol and/or dimethyl ether and these are subsequently converted to gasoline.

In particular, a typical GTL diesel plant consists of the following main process units: (a) air separation, (b) syngas preparation via ATR, (c) Fischer-Tropsch synthesis of a raw product of wax and liquid, (d) upgrading comprising hydrocracking and other refinery steps.

In most GTL diesel plants the main final products are diesel, kerosene, naphtha and liquid petroleum gas (LPG). In some GTL diesel plants higher value products such as lube oil are also produced. The value of the naphtha is lower than the diesel and LPG value is in most cases lower than the naphtha. In some geographic locations the LPG (mainly C3/C4 fraction) and other constituents of the light-end stream can have a very low value and limited market, hence the investment which has to be made into the upgrading of the light-end stream can be high compared with the value of the product. It is therefore known to recycle LPG to the reforming section of the plant.

WO2004/000772 concerns a process for production of a blended syngas feed. A first syngas (synthesis gas) is formed by reacting methane with oxygen, while a second syngas is formed using LPG and $CO_2$.

AU 20073566234 (WO2009/008092) discloses the recycle of a light-end fraction. According to this citation, LPG together with naphtha can be recycled into the syngas production step. This citation discloses hydrotreating of the Fischer-Tropsch product in the upgrading unit and does not require use of oxygen in the reforming stage, i.e. the synthesis gas producing unit is not an autothermal reformer but a steam methane reformer. Further, a particular and expensive catalyst in the form of supported ruthenium is used in order to avoid deactivation of the catalyst due to deposition of carbon derived from the recycle of the light-end fraction. In particular, the number of carbon atoms in the recycle light-end fraction stream is kept at 10-35% based on the number of carbon atoms of the natural gas fed to the synthesis gas producing unit, since at above 35% carbon deposition on the catalyst will take place. Below 10% it is stated that it is not possible to improve the raw material consumption.

WO2007/101831 discloses a process for the preparation of a Fischer-Tropsch (FT) synthesis product. After pre-reforming and partial oxidation, a syngas enters an FT synthesis. The FT product is separated into heavy and light streams, and the light stream (comprising inerts, $CO_2$ and $C_1$-$C_3$ hydrocarbons) is recycled. A portion of the light stream is recycled to the pre-reformer and a portion is recycled to the burner of the partial oxidation step. However, such light stream of unconverted syngas, inerts, $CO_2$ and C1-C3 is what is normally known as FT tail gas; it is not the light-end fraction, in particular LPG, from an upgrading unit downstream FT synthesis. In addition, the light stream (tail gas) of this citation leads at least a portion of it directly to the burner of a non-catalyzed partial oxidation reactor.

WO01/60773 discloses a system and method for operating a GTL plant. In involves pre-reforming, syngas generating via e.g. autothermal reforming, FT synthesis and product upgrading steps. Light fractions from the upgrading stage, which includes hydrotreating and/or hydroisomerization, are recycled into the pre-reformer (line 162, FIG. 2). However, such light fractions are fed back precisely to the pre-reformer and after addition of steam. This can result in sulphur poisoning of the pre-reformer catalyst as well as catalyst deactivation due to carbon deposition as a result of the presence of olefinic hydrocarbons.

WO2013/033812 and US2013/0065974 disclose a process for the production of diesel via Fischer-Tropsch synthesis in which naphtha from the upgrading section is recycled as ATR feed through a pretreatment unit to which steam and hydrogen are added. Such unit may include a feed gas hydrotreater, sulphur removal and a pre-reformer and combined with natural gas feed. There is no disclosure of the recycle of light-end fractions, in particular LPG to the hydrocarbon feed, e.g. natural gas feed.

It would be desirable to provide a process that overcomes the shortcomings of the above known processes.

SUMMARY OF THE INVENTION

According to the present invention as recited in the appended claims, a process for the production of liquid hydrocarbons from a hydrocarbon feedstock is provided.

The process comprises the first step of:

(a) combining a light-end fraction stream from the upgrading stage of step (g) with a stream of natural gas to form said hydrocarbon feedstock;

By the term "hydrocarbon feedstock" is meant a stream used in the process which comprises hydrocarbons. In the broadest sense, hydrocarbons are organic compounds comprising hydrogen and carbon. The hydrocarbons may be as simple as e.g. methane $CH_4$, and may comprise more complex molecules. The natural gas stream is a conventional feed having methane as its major constituent.

By the term "light-end fraction" is meant an off-gas from the upgrading stage (refinery stage) of Fischer-Tropsch, or gasoline synthesis, and which contains a wide range of constituents including hydrogen, carbon dioxide, carbon monoxide, methane, water, C1-C6 including C2-C6 fraction as well as C6+ constituents either as paraffins or olefins. The light-end fraction may comprise liquefied petroleum gas (LPG).

Step (b) of the process of the invention involves:

(b) passing said hydrocarbon feedstock through a hydrogenation stage to form a hydrogenated feedstock.

The present invention enables the elimination or reduction of the amount of external hydrogen needed in the hydrogenation of step (b) as the invention takes advantage of the hydrogen already present in the light-end fraction stream from the upgrading stage.

Hence, preferably the hydrogenation of step (b) is conducted without the addition of hydrogen to the hydrocarbon feedstock.

In the hydrogenation stage, part or all of the unsaturated hydrocarbons such as olefins are converted into paraffins according to the following reaction (given for olefins);

$$C_nH_{2n}+H_2 \leftrightarrow C_nH_{2n+2} \text{ (for } n \geq 2) \tag{1}$$

The olefins are hydrogenated over a CoMo or NiMo hydrogenation catalyst. The hydrogenation of olefins reduces the potential for i.a. carbon laydown in downstream units, particularly the pre-reformer. Further, the hydrogenated stream is prepared for the subsequent desulfurization stage, i.e. hydrodesulfurization.

Hence, step (c) of the process of the invention involves:

(c) passing the hydrogenated feedstock through a desulfurization stage to form a desulfurized feedstock.

Sulphur traces in the gas are thereby removed over a catalyst bed comprising zinc oxide, thereby avoiding sulphur poisoning of the pre-reformer downstream as well as other downstream catalysts such as the Fischer-Tropsch synthesis catalyst.

Step (d) of the process of the invention involves:

(d) passing the desulfurized feedstock through a pre-reforming stage under the addition of steam to form a pre-reformed gas.

The desulfurized feedstock is subjected to a step of pre-reforming, preferably adiabatic pre-reforming before being directed to downstream reforming stage. In the adiabatic pre-reformer most or all of the higher hydrocarbons (hydrocarbon compounds with 2 or more carbon atoms) are converted according to the following reactions:

$$C_nH_m+nH_2O \rightarrow (\tfrac{1}{2}m+n)H_2+nCO \tag{2}$$

$$3H_2+CO \leftrightarrow CH_4+H_2O \tag{3}$$

$$CO+H_2O \leftrightarrow H_2+CO_2 \tag{4}$$

Reactions (3) and (4) are normally close to equilibrium at the outlet of the pre-reformer.

Preferably, the pre-reforming stage is conducted adiabatically in a fixed bed of nickel catalyst. Thus, the adiabatic pre-reformer contains preferably a fixed bed of catalyst having nickel as the active constituent on a suitable carrier, such as MgO/A1203 or Mg—Al spinel.

Contrary to the prior art, the invention enables the use of relatively inexpensive nickel catalysts in the pre-reformer and downstream reforming stages, as the risk of carbon laydown or deposition and sulphur poisoning are mitigated upstream after the light-end fraction stream has combined with the natural gas stream.

Step (e) of the process of the invention involves:

(e) passing the pre-reformed gas through an Autothermal reformer (ATR) or Catalytic Partial Oxidation unit (CPO) under the addition of an oxidant gas to form a synthesis gas.

Autothermal reforming (ATR) is described widely in the art and open literature. Typically, the autothermal reformer comprises a burner, a combustion chamber, and catalyst arranged in a fixed bed all of which are contained in a refractory lined pressure shell. Autothermal reforming is for example described in Chapter 4 in "Studies in Surface Science and Catalysis", Vol. 152 (2004) edited by Andre Steynberg and Mark Dry.

In the ATR, oxidant gas, and in some cases steam is added. Synthesis gas ("syngas") is formed by a combination of steam reforming and partial oxidation in the autothermal reformer.

By the term "oxidant gas" is meant a stream comprising oxygen, preferably more than 75 vol %, more preferably more than 85 vol % oxygen. Examples of oxidant gas are air, oxygen, mixture of oxygen and steam, and oxygen enriched air.

The synthesis gas leaving the ATR is free of oxygen and the temperature of this hot effluent gas from the ATR is between 900 and 1100° C., or 950 and 1100° C., typically between 1000 and 1075° C. The hot effluent synthesis gas leaving the autothermal reformer comprises carbon monoxide, hydrogen, carbon dioxide, steam, residual methane, and various other components including nitrogen and argon.

Preferably the reforming step (e) is conducted without the use of Steam Methane Reformer (SMR) (tubular reformer). The use of ATR or CPO instead of the SMR has the advantage in first of all production of a syngas with the best sutiable syngas ratio $H_2/CO$ for the hydrocarbon synthesis, i.e. close to 2.0 for FT synthesis. An SMR will produce surplus of $H_2$ due to the need of operating at high S/C ratios, normally well above 1.1, for instance 1.5 or higher, as well as with high $CO_2$ and $CH_4$ in the syngas which act as inerts in the hydrocarbon synthesis. In addition, the investment of an ATR based plant is lower than the SMR plant for the same amount of CO in the syngas.

Step (f) of the process of the invention involves:

(f) passing the synthesis gas through a Fischer-Tropsch synthesis stage to form a tail gas stream and a raw product stream of hydrocarbons.

In the Fischer-Tropsch synthesis the synthesis gas is converted to a raw stream of hydrocarbons basically in the form of wax and liquid, along with a tail gas containing unconverted synthesis gas. Tail gas is as used herein off-gas from Fischer-Tropsch synthesis which is not reused in this stage.

The final step (g) of the process of the invention involves:

(g) passing the raw product stream of hydrocarbons through an upgrading stage to form a final product stream of liquid hydrocarbons and a light-end fraction stream, in which the light-end fraction stream comprises a C1-C6 fraction and C6+ fraction containing paraffinic and olefinic hydrocarbons, but no naphtha.

The upgrading stage is a refinery stage in which the raw product stream of hydrocarbons is separated into individual components such as valuable diesel, as well as light-end fractions comprising LPG. In the present invention, this light-end fraction stream has no naphtha. Naphtha is a light-end fraction having hydrocarbons in the range C5-C10 or C4-C10 with main hydrocarbons in the C4-C9 range.

According to the present invention, the light-end fraction is recycled back to a point in the process which is well before pre-reforming, i.e. before steam addition and even before desulfurization. Hence, the risk of carbon laydown or deposition as well as sulphur poisoning in the pre-reformer and downstream synthesis units is reduced, while at the same time it is possible to obtain better carbon utilization in the overall process as well as lower natural gas consumption per unit of diesel product.

It has been found that the compared to light-end fractions such as LPG, the recycle of naphtha to the natural gas, despite reducing the amount of natural gas import and thus improving carbon utilization, results in lower process economy (higher capital costs). By recycling naphtha there is a need to operate the reforming section at a higher steam-to-carbon molar ratio to avoid carbon formation which conveys carrying more steam in the process and thus also a significant increase in tail gas addition in order to keep the $H_2/CO$ molar ratio in the synthesis gas at the desired level of about 2. In addition, the higher steam-to-carbon leads to higher inlet flow to pre-reformer and ATR. The higher flow in the ATR, in particular, implies that more oxygen is required thus resulting in significant higher investments in the air separation plant used to produce the oxygen.

The present invention enables therefore a better carbon utilization (less natural gas import) while at the same time providing a better process economy than the prior art.

In conventional Fischer-Tropsch processes, hydrotreating is conducted as part of the upgrading stage. In the present invention, the hydrotreatment is in a way provided via the hydrogenation stage upstream the desulphurization and pre-reforming stage, thus completely independent from the upgrading stage of the Fischer-Tropsch section, and rather as a part of the reforming section of the process while at the same time reducing or eliminating the use of external hydrogen in the hydrogenation stage.

In addition, the present invention reduces/eliminates the amount of equipment in the upgrading stage that otherwise would be required to upgrade the light-end stream. The alternative to upgrading is that this stream end as fuel-gas, which reduces the overall carbon efficiency of the plant.

In a particular embodiment in connection with one of the above or below embodiments, the upgrading stage (g) comprises hydrocracking but no hydrotreating.

In hydrocracking a catalyst such a zeolite is provided in order to cut C-C bonds; hence hydrocracking changes the boiling point of the liquid hydrocarbons or shorten the carbon length. In hydrotreating, the catalysts are different and the process is rather used for selective addition of hydrogen to saturate olefins and aromatics. The ranges of temperatures and pressures are also more moderate than in hydrocracking processes.

In a particular embodiment in connection with one or more of the above or below embodiments, the entire light-end stream is used in step (a). Hence, according to this particular embodiment the light-end stream is not divided but provided in its entirety into step (a), i.e. to the natural gas or other suitable feedstock prior to hydrodesulphurization and steam addition.

In a particular embodiment in connection with one or more of the above or below embodiments, the light-end fraction stream comprises a C1-C6 fraction and C6+ fraction containing paraffinic and olefinic hydrocarbons. Preferably the light-end fraction has a composition:

| | | |
|---|---|---|
| H2 | 29 | mole % |
| CO | 4 | mol % |
| CO2 | 11 | mole % |
| CH4 | 6 | mol % |
| N2 | 1 | mole % |
| C2 | 3 | mole % |
| C3 | 8 | mole % |
| C4 | 18 | mole % |
| C5 | 9 | mole % |
| C6+ | 6 | mole % |
| H20 | 5 | mole % | in which a minor fraction of the hydrocarbons are olefins while the majority of the hydrocarbon fraction are paraffins. Further the stream may contain traces of sulphur components.

The light-end fraction stream may also comprise LPG, as defined below.

In another particular embodiment the light-end fraction stream is liquefied petroleum gas (LPG) constituted by a C2-C6 fraction, preferably having propane, butane, propylene and butylene (C3-C4) as its major constituents, where this C3-C4 fraction represents at least 95 mole %, preferably at least 95 mole %.

Preferably the LPG stream has the composition:

| | |
|---|---|
| C2 | 0.7 mole % |
| C3 | 28 mole % |
| C4 | 70 mole % |
| C5 | 1 mole % |
| C6 | 0.3 mole % |

In a particular embodiment in connection with one of the above or below embodiments, the hydrogenation of step (b) is conducted under the addition of hydrogen to the hydrocarbon feedstock. Such addition of external hydrogen may be required when the light-end fraction stream is LPG either having low or no hydrogen content.

In a particular embodiment in connection with one or more of the above embodiments, the ATR or CPO stage is conducted in a fixed bed of nickel catalyst in which the active component is not solely a metal of the group consisting or Rh, Ru, Ir, Pt and mixtures thereof. Accordingly, in the present invention the catalyst in the ATR or CPO is nickel based, i.e. nickel is an active constituent, optionally together with e.g. Ir, but because of the reduced risks of carbon deposition, there is no need of using expensive catalysts in which the active constituent is solely Rh, Ru, Ir, Pt or a mixture of these, in particular Ru as disclosed in AU 20073566234 (WO2009/008092).

In another particular embodiment in connection with one or more of the above embodiments, tail gas from the Fischer-Tropsch synthesis of step (f) is recycled to hydrogenation stage (b), desulphurization stage (c), pre-reforming stage (d), reforming stage (e), or a combination thereof. The addition of tail gas which is a $CO_2$-rich stream to the reforming section, preferably to the ATR or CPO in reforming stage (e), enables that there is sufficient carbon dioxide during the reforming stage to achieve the desired $H_2/CO$ molar ratio in the synthesis gas, typically about 2 for Fischer-Tropsch synthesis as described previously.

In another particular embodiment in connection with one or more of the above embodiments, step (e) further comprises passing the pre-reformed gas through a heat exchange reformer before the ATR or CPO, and using the hot effluent gas from the ATR or CPO as heat exchanging medium in the heat exchange reformer thereby cooling the hot effluent gas into said synthesis gas. The provision of the heat exchange reformer, preferably in series arrangement with the ATR or CPO, enables operation of the process at lower process steam-to-carbon molar ratios ($S/C_{process}$), e.g. at 0.4-1.3 often 0.6-1.1, and thereby reduction of equipment size downstream as there is less steam to be carried in the process.

The process steam-to-carbon ratio, $S/C_{process}$, means the number of moles steam divided by the number of moles of hydrocarbon carbon. The number of moles of steam includes all the steam added to the hydrocarbon feedstock upstream the heat exchange reformer. The hydrocarbon carbon means the hydrocarbons present in the feedstock and includes the hydrocarbon carbon from the recycled light-end fraction. The $S/C_{process}$ ratio is measured upstream the heat exchange reformer, or upstream the pre-reformer.

There are other hydrocarbon synthesis than Fischer Tropsch for which the invention applies-suitably in the form of hydrocarbon synthesis processes for gasoline production involving methanol and/or dimethyl ether (DME) as intermediate building blocks, i.e. oxygenates, as for instance disclosed in our U.S. Pat. Nos. 4,520,216 and 4,481,305. In such processes there is also a light-end fraction stream from particularly the product upgrading stage (cleaning section) which may be recycled to the syngas section comprising the reforming stages, specifically to the produced synthesis gas, or to the gasoline synthesis in order to increase the carbon efficiency and limit the amount of hydrocarbons that ends as fuel in the hydrocarbon synthesis plant. In the reforming stage, a heat exchange reformer or Steam Methane Reformer (SMR) may suitably be combined with an ATR or secondary reformer (where enriched air, normally about 44% oxygen is added) to produce the syngas used in downstream production of methanol and/or DME as intermediate products (oxygenates) to the subsequent gasoline synthesis and final product upgrading.

US2010/0036186 discloses also a process for the production of liquid hydrocarbons in the gasoline range in which the effluent from a gasoline synthesis reactor is passed to a separation stage, whereby gasoline is separated together with LPG. An unconverted stream of unconverted gas lighter hydrocarbons is recycled to oxygenate synthesis reactor and synthesis stage located upstream. There is no disclosure of the recycle of LPG to the hydrocarbon feed, e.g. natural gas feed.

Accordingly, as recited in the appended claims the invention provides also a process for the production of liquid hydrocarbons in the form of gasoline from a hydrocarbon feedstock containing natural gas comprising:

(i) combining a light-end fraction stream from the upgrading stage of step (vii) with a stream of natural gas to form said hydrocarbon feedstock;

(ii) passing said hydrocarbon feedstock through a hydrogenation stage to form a hydrogenated feedstock;

(iii) passing the hydrogenated feedstock through a desulfurization stage to form a desulfurized feedstock;

(iv) passing the desulfurized feedstock through a pre-reforming stage under the addition of steam to form a 0pre-reformed gas;

(v) passing the pre-reformed gas through an autothermal reformer (ATR), secondary reformer or Catalytic Partial Oxidation unit (CPO) under the addition of an oxidant gas to form a synthesis gas;

(vi) passing the synthesis gas through a methanol synthesis stage, dimethyl ether (DME) synthesis stage, or a combination of both, to form a raw product stream of oxygenates comprising methanol, DME or a mixture of both;

(vii) passing the raw product stream of oxygenates through a gasoline reactor to form a raw product stream of gasoline and passing said raw product stream through an upgrading stage to form a final product stream of liquid hydrocarbons comprising gasoline and a light-end fraction stream, in which the light-end fraction stream is liquefied petroleum gas (LPG) constituted by a C2-C6 fraction.

It would be understood that in step (vii) the gasoline reactor produces a product effluent which is cooled to provide separate effluents of water, a tail gas (unconverted gas) which is rich in $CO_2$, as well as a liquid hydrocarbon phase of mixed gasoline and a light-end fraction in the form of LPG, i.e. raw product stream of gasoline or simply raw gasoline. The raw gasoline may be further processed by conventional means to obtain a lower-boiling gasoline fraction and the light-end fraction as LPG. Normally, LPG is not recycled to the reforming section of the plant, in particular to the hydrocarbon feed, e.g. natural gas feed.

In a particular embodiment tail gas from the gasoline reactor of step (vii), in particular from the upgrading stage of step (vii), is recycled to hydrogenation stage (ii), desulphurization stage (iii), pre-reforming stage (iv), reforming stage (v), or a combination thereof. Preferably, the tail gas is recycled to the gasoline reactor of step (vii).

In a particular embodiment in connection with the above or below embodiments, step (v) further comprises passing the pre-reformed gas through:

a heat exchange reformer before the ATR, secondary reformer or CPO, and using the hot effluent gas from the ATR, secondary reformer or CPO as heat exchanging medium in the heat exchange reformer thereby cooling the hot effluent gas into said synthesis gas, or a steam methane reformer (SMR) before the ATR, secondary reformer or CPO.

In another particular embodiment in connection with any of the above or below embodiments, the upgrading stage (vii) comprises hydrocracking but no hydrotreating.

In yet another particular embodiment in connection with any of the above embodiments, step (ii) is conducted under the addition of hydrogen to the hydrocarbon feedstock.

BRIEF DESCRIPTION OF THE FIGURES

The invention is further illustrated by reference to the attached FIGURE which shows a specific embodiment of the invention in which LPG recycle is used in the syngas section (reforming section) of a GTL plant, upstream the hydrogenation stage and before steam addition.

DETAILED DESCRIPTION

Referring to the appended FIGURE, a hydrocarbon feedstock 3 is formed by combining natural gas 1 with LPG recycle stream 2 from downstream upgrading unit of Fischer-Tropsch section for producing diesel or downstream synthesis section for production of gasoline (not shown). Hydrogen 4 is added to the hydrocarbon feedstock prior to heating in fired heater 30 using fuel source 7. The heated hydrocarbon feed is then passed through hydrogenation reactor 40 containing a fixed bed 41 of CoMo or NiMo catalyst, then hydrodesulphurization unit (HDS) 50 containing a fixed bed 51 comprising ZnO to capture sulphur. The desulphurized feedstock 5 is then passed through adiabatic pre-reformer 60 containing a fixed bed of nickel catalyst 61 under the addition of steam 6 and further heating via fired heater 30. The pre-reformed 8 gas is further heated and is combined with a CO2-rich recycle stream 9 such as Fischer-Tropsch tail gas to form stream 10. The pre-reformed gas stream 10 is then passed through autothermal reformer (ATR) 70 comprising a bed of nickel based catalyst 71. Oxygen 11 and steam 12 may be added to form a mixture 13 of oxygen and steam which is supplied to ATR 70. Oxygen 13 and steam 12 can also be supplied independently. The hot effluent gas 14 from the ATR is then cooled in waste heat boilers 80, 81 under the production of high pressure steam 15 using boiler feed water 16. The cooled synthesis gas 17 is then passed through a final cooling and separation stage 90, where water 18 (process condensate) is removed and synthesis gas stream 19 is produced for downstream process, such as Fischer-Tropsh synthesis for production of diesel, or methanol and/or DME followed by gasoline synthesis for production of gasoline.

EXAMPLE 1

In one embodiment a light-end fraction stream containing LPG components and other light gasses are withdrawn from separation step which could be a stripper column in the upgrading section. An example of light-end fraction stream composition is listed below:

| | |
|---|---|
| H2 | 29 mole % |
| CO | 4 mol % |
| CO2 | 11 mole % |
| CH4 | 6 mol % |
| N2 | 1 mole % |
| C2 | 3 mole % |
| C3 | 8 mole % |
| C4 | 18 mole % |
| C5 | 9 mole % |
| C6+ | 6 mole % |
| H20 | 5 mole % |

A minor fraction of the hydrocarbons are olefins while the majority of the hydrocarbon fraction is paraffins. Further the stream could contain traces of sulphur components.

The light-end stream containing LPG is recycled to the desulphurization reactor of the syngas section in which it is mixed with a natural gas stream. The olefins in the combined gas stream are hydrogenated over a hydrogenation catalyst under the addition of hydrogen (typical CoMo og NiMo type catalyst) thereby removing undesirable olefins and any sulphur components in the combined gas are then removed on the desulphurization catalysts of the subsequent desulphurization stage. The light-end stream containing LPG stream substitutes some of the natural gas fed to the process. The hydrogenated and sulphur depleted feed gas is then mixed with steam and sent to the pre-reformer followed by the ATR reformer.

As an example from a GTL plant an light-end stream with a flow of totally of 224 Nm$^3$/hr (with above composition) is recycled back to the syngas section, in particular upstream the hydrogenation stage. Despite of the low recycle ratio of the light-end stream, i.e. about 2% of the natural gas feed, the amount of natural gas (NG) import is reduced by 3% from 11378 Nm$^3$/hr to 11035 Nm$^3$/hr. The syngas section continue to produce the same amount of syngas with the desirable H$_2$/CO molar ratio=2.0 for Fischer-Tropsch synthesis, in an amount of 33700 Nm$^3$/hr which is equivalent to a liquid production of approx 1000 BPD while at the same time avoiding sulphur poisoning as well as carbon deposition of the pre-reformer. The pre-reformer and the autothermal reformer can be operated with conventional nickel catalysts, i.e. without the need of using expensive catalysts based on Ru, Rh, Ir, or Pt as the sole active constituents.

EXAMPLE 2

In another embodiment the light-end gas from a separation step which could be a stripper column in the upgrading section has been further separated into a light end fuel gas and a LPG stream.

The LPG stream has the following composition:

| | |
|---|---|
| C2 | 0.7 mole % |
| C3 | 28 mole % |
| C4 | 70 mole % |
| C5 | 1 mole % |
| C6 | 0.3 mole % |

A minor fraction of the hydrocarbons are olefins while the majority of the hydrocarbon fraction is paraffins.

The LPG stream is recycled to the desulphurization reactor of the syngas section in which it is mixed with the other hydrocarbon feed stream, namely natural gas. The olefins in the LPG stream are hydrogenated over the hydrogenation catalyst (typically CoMo og NiMo type catalyst). The LPG stream substitutes some of the natural gas coming (or other hydrocarbon feed stream coming from outside feed source). The hydrogenated and sulphur depleted feed gas is then mixed with steam and sent to the pre-reformer followed by the ATR reformer.

As an example from a GTL plant a LPG recycle stream of 224 Nm$^3$/hr (with above composition) is recycled back to the syngas section, upstream the hydrogenation stage. Despite the low recycle ratio of LPG with respect to natural gas (about 2%), the amount of natural gas (NG) import is reduced by 5% from 11378 Nm3/hr to 10805 Nm3/hr. The syngas section continue to produce the same amount of syngas with the desired H$_2$/CO molar ratio=2.0 for Fischer-Tropsch synthesis in an amount of 33796 Nm$^3$/hr which is equivalent to a liquid production of approx 1000 BPD while at the same time avoiding sulphur poisoning as well as carbon deposition of the pre-reformer. As Example 1, the pre-reformer and the autothermal reformer can be operated with conventional nickel catalysts, i.e. without the need of using expensive catalysts based on Ru, Rh, Ir, or Pt as the sole active constituents.

EXAMPLE 3

Comparative

In another embodiment a light hydrocarbon fraction which is separated from the main hydrocarbon fraction in a separation step in a fractionation column. The main hydrocarbon fraction is a diesel fraction and the light end fraction is a naphtha fraction. The naphtha fraction is recycled to the syngas section and mixed with the other hydrocarbon feed upstream the desulphurization stage.

The naphtha stream contains long chain higher hydrocarbons and the syngas section must be operated at higher steam-to-carbon ratio to avoid carbon formation from the higher hydrocarbons in the reforming section and especially in the pre-reforming step. This will require a higher addition of high pressure steam to the hydrocarbon feed and thereby higher steam consumption. Most of the equipment will increase in size and thereby in cost due to the high steam-to-carbon molar ratios.

The naphtha stream is a stream with initial boiling point of 30° C. and final boiling point of 170° C. with main hydrocarbon in the C4-C9 range.
Naphtha Composition:

| Components | Mole % |
|---|---|
| C4 | 1.1 |
| C5 | 12.5 |
| C6 | 21.5 |
| C7 | 32.6 |
| C8 | 25.8 |
| C9 | 7.6 |

As an example from a GTL plant a naphtha recycle stream of 650 kg/hr (with above composition) is recycled back to the syngas section. The amount of natural gas (NG) import is reduced by 19% from 11378 Nm$^3$/hr to 9193 Nm$^3$/hr, which improves carbon utilization, yet at the same time the recycle of Fischer-Tropsch tail gas increases by a factor 1.5-2 because of the naphtha process require operating at a higher steam-to-carbon ratio. The increase in the flow of such tail gas is needed to compensate for the higher steam-to-carbon ratio in order to obtain the desired $H_2/CO$ molar ratio of 2 in the synthesis gas used for Fischer-Tropsch synthesis. Accordingly, the costs of the tail gas recycle compressor increases. Since the higher steam-to-carbon ratio leads to higher inlet flow to the pre-reformer and ATR, a higher oxygen requirement in the ATR is necessary. The amount of oxygen import increases by 7% resulting in an associated increase in the investment of the air separation plant. The total flow through the plan increases and thereby most equipment will increase in size by 9%, with an associated increase in equipment cost. The syngas section continue to produce the same amount of syngas with $H_2/CO$ ratio=2.0 in an amount of 33796 $Nm^3/hr$. Even though the natural gas consumption is reduced by 19% the operation cost and investment increases. This example illustrates that the recycle of naphtha is not beneficial to the process economy or the investment in the syngas section of the GTL plant, despite savings in carbon utilization in the form of reduced NG import.

The invention claimed is:

1. Process for the production of liquid hydrocarbons from a naphtha free hydrocarbon feedstock comprising:
    (a) passing a hydrocarbon feedstock through a hydrogenation stage to form a hydrogenated feedstock;
    (b) passing the naphtha free hydrogenated feedstock through a desulfurization stage to form a desulfurized feedstock;
    (c) passing the desulfurized feedstock through a pre-reforming catalytic nickel stage under the addition of steam to form a pre-reformed gas;
    (d) passing the pre-reformed gas through an autothermal reformer (ATR) or Catalytic Partial Oxidation unit (CPO) under the addition of an oxidant gas to form a synthesis gas;
    (e) passing the synthesis gas through a Fischer-Tropsch synthesis stage to form a tail gas stream and a raw product stream of hydrocarbons;
    (f) passing the raw product stream of hydrocarbons through an upgrading stage to form a final product stream of liquid hydrocarbons and a naphtha free light-end fraction stream, the naphtha free light-end fraction stream comprises a C1-C6 fraction and C6+ fraction containing paraffinic and olefinic hydrocarbons, but no naphtha, wherein said naphtha free light-end fraction stream is combined with a stream of natural gas to form the naphtha free hydrocarbon feedstock.

2. Process according to claim 1 in which the upgrading stage (f) comprises hydrocracking but no hydrotreating.

3. Process according to claim 1 in which the naphtha free light-end fraction stream is liquefied petroleum gas (LPG) constituted by a C2-C6 fraction.

4. Process according to claim 1 in which the hydrogenation of step (a) is conducted under the addition of hydrogen to the naphtha free hydrocarbon feedstock.

5. Process according to claim 1 in which the pre-reforming stage is conducted adiabatically in a fixed bed said catalytic of nickel catalyst.

6. Process according to claim 1 in which the ATR or CPO stage is conducted in a fixed bed of nickel catalyst in which the active component is not solely a metal of the group consisting or Rh, Ru, Ir, Pt and mixtures thereof.

7. Process according to claim 1 in which tail gas from the Fischer-Tropsch synthesis of step (e) is recycled to hydrogenation stage (a), desulphurization stage (b), pre-reforming stage (c), reforming stage (d), or a combination thereof.

8. Process according to claim 1 in which step (d) further comprises passing the pre-reformed gas through a heat exchange reformer before the ATR or CPO, and using the hot effluent gas from the ATR or CPO as heat exchanging medium in the heat exchange reformer thereby cooling the hot effluent gas into said synthesis gas.

9. Process for the production of liquid hydrocarbons in the form of gasoline from a naphtha free hydrocarbon feedstock containing natural gas comprising:
    (i) combining a naphtha free light-end fraction stream with a stream of natural gas to form the naphtha free hydrocarbon feedstock;
    (ii) passing said naphtha free hydrocarbon feedstock through a hydrogenation stage to form a hydrogenated feedstock;
    (iii) passing the hydrogenated feedstock through a desulfurization stage to form a desulfurized feedstock;
    (iv) passing the desulfurized feedstock through a pre-reforming stage under the addition of steam to form a pre-reformed gas;
    (v) passing the pre-reformed gas through an autothermal reformer (ATR), secondary reformer or Catalytic Partial Oxidation unit (CPO) under the addition of an oxidant gas to form a synthesis gas;
    (vi) passing the synthesis gas through a methanol synthesis stage, dimethyl ether (DME) synthesis stage, or a combination of both, to form a raw product stream of oxygenates comprising methanol, DME or a mixture of both;
    (vii) passing the raw product stream of oxygenates through a gasoline reactor to form a raw product stream of gasoline and passing said raw product stream through an upgrading stage to form a final product stream of liquid hydrocarbons comprising gasoline and a naphtha free light-end fraction stream, in which the light-end fraction stream is liquefied petroleum gas (LPG) constituted by a C2-C6 fraction.

10. Process according to claim 9 in which step (v) further comprises passing the pre-reformed gas through:
    a heat exchange reformer before the ATR, secondary reformer or CPO, and using the hot effluent gas from the ATR, secondary reformer or CPO as heat exchanging medium in the heat exchange reformer thereby cooling the hot effluent gas into said synthesis gas, or
    a steam methane reformer (SMR) before the ATR, secondary reformer or CPO.

11. Process according to claim 9 in which the upgrading stage (vii) comprises hydrocracking but no hydrotreating.

12. Process according to claim 9 in which step (ii) is conducted under the addition of hydrogen to the hydrocarbon feedstock.

* * * * *